US 7,708,683 B2

(12) United States Patent
Hadley

(10) Patent No.: US 7,708,683 B2
(45) Date of Patent: May 4, 2010

(54) METHODS FOR QUANTIFYING THE RISK OF CARDIAC DEATH USING EXERCISE INDUCED HEART RATE VARIABILITY METRICS

(75) Inventor: David M. Hadley, Woodinville, WA (US)

(73) Assignee: Cardiac Science Corporation, Bothell, WA (US)

( * ) Notice: Subject to any disclaimer, the term of this patent is extended or adjusted under 35 U.S.C. 154(b) by 438 days.

(21) Appl. No.: 11/681,099

(22) Filed: Mar. 1, 2007

(65) Prior Publication Data

US 2007/0208266 A1  Sep. 6, 2007

Related U.S. Application Data

(60) Provisional application No. 60/779,313, filed on Mar. 3, 2006.

(51) Int. Cl.
*A61N 1/00* (2006.01)
(52) U.S. Cl. ....................................................... 600/15
(58) Field of Classification Search ................ 340/576, 340/572.1; 600/515, 519; 702/181, 188, 702/189, 193; 375/130, 241
See application file for complete search history.

(56) References Cited

U.S. PATENT DOCUMENTS

| 5,148,812 | A | 9/1992 | Verrier et al. |
| 5,437,285 | A | 8/1995 | Verrier et al. |
| 5,682,900 | A | 11/1997 | Arand et al. |
| 5,713,367 | A | 2/1998 | Arnold et al. |
| 5,755,671 | A | * | 5/1998 | Albrecht et al. ............. 600/516 |
| 6,648,829 | B2 | 11/2003 | Starobin et al. |
| 7,136,694 | B2 | 11/2006 | Hadley et al. |
| 7,151,957 | B2 | 12/2006 | Beker et al. |
| 7,167,744 | B2 | 1/2007 | Hadley et al. |
| 7,167,745 | B2 | 1/2007 | Hadley et al. |
| 7,174,204 | B2 | 2/2007 | Hadley et al. |
| 2003/0013979 | A1 | 1/2003 | Dardik et al. |
| 2003/0149370 | A1 | 8/2003 | Starobin et al. |
| 2005/0038351 | A1 | 2/2005 | Starobin et al. |
| 2005/0065443 | A1 | 3/2005 | Ternes |
| 2005/0222513 | A1 | 10/2005 | Hadley et al. |
| 2007/0249949 | A1 | 10/2007 | Hadley |

OTHER PUBLICATIONS

U.S. Appl. No. 11/733,699, filed Apr. 10, 2007, Hadley.
Arai Y, Saul JP, Albrecht P, Hartley LH, Lilly LS, Cohen RF, and Colucci W., *Modulation of Cardiac Autonomic Activity During and Immediately After Exercise*, Am.J.Physiol. 1989, H132-H141.

(Continued)

*Primary Examiner*—George Manuel
*Assistant Examiner*—Robert N Wieland
(74) *Attorney, Agent, or Firm*—Patterson, Thuente, Skaar & Christensen, P.A.

(57) ABSTRACT

Methods and apparatus for assessing cardiac risks in a specific patient. One embodiment of a method in accordance with the invention comprises providing heart rate activity of a specific patient including a windowed time series relating to heart rate variability during a heart rate test. This method further includes determining a frequency domain value based on energy values of frequency bands of the heart rate variability in the windowed time series, and/or determining an aggregate power for a frequency band of the windowed time series. This method further includes assessing the risk of a cardiac event based on the frequency value and/or the aggregate power.

35 Claims, 10 Drawing Sheets

OTHER PUBLICATIONS

Van Ravenswaaij CMA, Kollee LAA, Hopman JCW, Stoelinga GBA, and van Geijn HP, *Heart Rate Variability*, Annals of Internal Medicine 1993, 118(6): 435-447.

Nolan J, et al., *Prospective Study of Heart Rate Variability and Mortality in Chronic Heart Failure*, Circulation 1998, 98:1510-1516.

Eckberg DL, *Sympathovagal Balance—A Critical Appraisal*, Circulation 1997; 96:3224-3232.

Kannankeril PJ, and Goldberger JJ, *Parasympathetic Effects on Cardiac Electrophysiology During Exercise and Recovery*, AM J Physiol Heart Circ. Physiol 2002; 282:H2091-H2098.

Tsuji H, Larson MG, Venditti FG, Manders ES, Evans JC, Feldman CL, and Levy D, *Impact of Reduced Heart Rate Variability on Risk for Cardiac Events—The Framingham Heart Study*, Circulation 1996, 94:2850-2855.

Chiou CW, and Zipes DP, *Selective Vagal Denervation of the Atria Eliminates Heart Rate Variability and Baroreflex Sensitivity While Preserving Ventricular Innervation*, Circulation 1998; 98:360-368.

Goldberger JJ, Challapalli S, Tung R, Parker MA, and Kadish AH, *Relationship of Heart Rate Variability to Parasympathetic Effect*, Circulation 2001, 103:1977-1983.

Goldberger JJ, Ahmed MW, Parker MA, and Kadish AH, *Dissociation of Heart Rate Variability from Parasympathetic Tone*, Am. J. Physiol. 1994; 266:H2152-H2157.

Pichon AP, de Bisschop C, Roulaud M, Denjean A, and Papelier Y, *Spectral Analysis of Heart Rate Variability During Exercise in Trained Subjects*, Med. Sci. Sports Exerc. 2004, 36(10):1702-1708.

Zipes DP and Wellens Hjj. *Sudden Cardiac Death*. Circulation. 1998;98:2334-2351.

Schwartz PG, La Rovere MT an Vanoli E. *Autonomic Nervous System and Sudden Cardiac Death*. Circulation. 1992;85(suppl 1):1-77-1-91.

Imai K, Sato H., Hori M, Kusuoka H, Ozki H, Yokoyama H, Takeda H, Inoue M, and Kamada T. *Vagally Mediated Heart Rate Recovery After Exercise is Accelerated in Athletes but Blunted in Patients With Chronic Heart Failure*. JACC. 1994; 24(6):1529-35.

Kannankeril PJ, Le FK, Kadish Ah and Goldberger JJ. *Parasympathetic Effects on Heart Rate Recovery After Exercise*. J Investigative Med. 2004;52(6):394-401.

Nishime EO, Cole CR, Blackstone EH, Pashkow FJ, and Luer MS. *Heart Rate Recovery and Treadmill Exercise Score as Predictors of Mortality in Patients Referred for Exercise ECG*. JAMA. 2000; 284(11):1392-8.

Cole CR, Foody JM, Blackstone EH and Lauer MS. *Heart rate recovery after Submaximal Exercise Testing as a predictor of Mortality in Cardiovascularly Healthy Cohort*. Ann Intern Med. 2000;132:552-555.

Shelter K, Marcus R, Froelicher VF, Vora S, Kalisetti D, Prakash M, Do D, and Myers J. *Heart Rate Recovery: Validation and Methodologic Issues*. JACC. 2001; 38(7):1980-7.

Nissinen SI, Makikallio TH, Seppanen T, Tapanainen JM, Salo M, Tulppo MP and Huikuri HV. *Heart Rate Recovery After Exercise as a Predictor of Mortality Among Survivors of Acute Myocardial Infarction*. AM J. Cardiol. 2003; 91:711-4.

Mark DB, Shaw L, Harrell FE, Hlatky MA, Lee KL, Bengtson JR, McCants CB, Califf RM and Pryor DB. *Prognostic Value of a Treadmill Exercise Score in Outpatients With Suspected Coronary Artery Disease*. N Eng. J Med. 1991;325(12):849-53.

Cole CR, Blackstone EH, Pashkow FJ, Snader CE and Lauer MS. *Heart-Rate Recovery Immediately After Exercise as a Predictor of Mortality*. N Eng J Med. 1999;341:1351-7.

Morshedi-Meibodi A, Larson MG, Levy D, O'Donnell CJ, Vasan RS. *Heart Rate Recovery After Treadmill Exercise Testing and Risk of Cardiovascular Disease Events (The Framingham Heart Study)*. Am J. Cardiol. 2002; 90:848-52.

Vivekananthan DP, Blackstone EH, Pothier CE, and Lauer MS. *Heart Rate Recovery After Exercise Is a Predictor of Mortality, Independent of the Angiographic Severity of Coronary Disease*. J. Am. College Cardiology. 2003; 42(5):831-8.

Mora S, Redberg RF, Cui Y, Whiteman MK, Flaws JA, Sharrett AR, and Blumenthal RS. *Ability of Exercise Testing to Predict Cardiovascular and All-Cause Death in Asymptomatic Women*. JAMA. 2003; 290(12)1600-7.

Racine NR, Blanchet M, Ducharme A, Marquis J, Boucher JM, Juneau M and White M. *Decreased Heart Rate Recovery After Exercise in Patients With Congestive Heart Failure: Effect of Beta-Blocker Therapy*. J. Cardiac Failure. 2003; 9(4):296-302.

Gibbons R. *Commentary: Abnormal Heart-Rate Recovery After Exercise*. The Lancet. 2002; 359:1536-7.

Desai M, De la Pena-Almaguer E, and Mannting F. *Abnormal Heart Rate Recovery After Exercise as a Reflection of an Abnormal Chronotropic Response*. Am J. Cardiol. 2001; 87:1164-1169.

Franklin, JN. *Well-posed stochastic extension of ill-posed linear problems*. J. Math. Anal. Appl. 1970; 31:682-716.

Wiggins, RA. *The general linear inverse problem: Implications of surface waves and free oscillations for earth structure*. Rev. Geophys and Space Phys. 1972; 10:251-285.

International Search Report and Written Opinion for PCT/US2007/066349, mailed Dec. 26, 2007.

Takashi, y. et al. *Characteristics of Heart Rate Decay Regulated by Neural Component after Dynamic Exercise in Athletes*. (1999) Respiration and Circulation. vol. 47, No. 6. pp. 627-633.

Lipinski, M.J. et al. *Novel Heart Rate Recovery Constant Predicts the Presence and Severity of Coronary Artery Disease*. (2003) Journal of the American College of Cardiology. vol. 41, No. 6. pp. 166 and Lauer, M.S. et al. *Timing of Heart Rate Decay After Exercise and Mortality*. (2003) Journal of the American College of Cardiology. vol. 41, No. 6.

File History for U.S. Appl. No. 11/733,699, filed Apr. 10, 2007.

Cook NR., "Use and misuse of the receiver operating characteristic curve in risk prediction", *Circulation*, 2007;115:928-35.

Jouven X, Empana J-P, Schwartz PJ, Desnos M, Courbon D, Ducimetiere P., "Heart-Rate profile during exercise as a predictor of sudden death", *n Engl J Med.*, 2005;352:1951.

Lauer MS, Okin PM, Larson MG, Evans JC, D Levy, "Impaired heart rate response to graded exercise: prognostic implications of chronotropic incompetence in the Framingham Heart Study", *Circulation*, 1996;93:1520.

Myers J, Bader D, Madhavfen R, Froelicher V., "Validation of a specific activity questionnaire to estimate exercise tolerance in patients referred for exercise testing", *Am Heart J.*, 2001;142:1041.

International Search Report and Written Opinion for International Application No. PCT/US07/63096, mailed Mar. 3, 2008.

* cited by examiner (A)

(B)

Spectral Bands:
Low: [0.04 – 0.15 Hz]; Mid: [0.15 – 0.40 Hz]; High: [0.40 – 1.0 Hz]

METHODS FOR QUANTIFYING THE RISK OF CARDIAC DEATH USING EXERCISE INDUCED HEART RATE VARIABILITY METRICS

CROSS-REFERENCE TO RELATED APPLICATION

This application claims the benefit of U.S. Provisional Patent Application No. 60/779,313 filed Mar. 3, 2006, which is herein incorporated by reference.

TECHNICAL FIELD

The present invention relates to methods and apparatus for assessing the risk of death from cardiovascular causes using spectral and temporal characterizations of heart rate variability from heart rate measurements made during cardiac stress testing.

BACKGROUND

Sudden cardiac death (SCD) accounts for approximately 300,000-400,000 deaths per year in the United States. Although the individual risk of SCD in the adult U.S. population is only about 0.1-0.2% per year, when applied to the large population base, SCD is often the first and only manifestation of the presence of a cardiovascular disease in a majority of cardiovascular related deaths. Deaths associated with recovering from large myocardial infarctions actually represent the minority of the total cardiovascular related deaths per year. As a result, a low cost screening tool that would provide early detection of patients at risk for SCD would be tremendously valuable for early treatment and intervention.

However, it can be difficult to accurately predict or assess the risk of SCD because many underlying pathologies support or trigger the events leading to SCD instead of any single condition. Of these various conditions, most data suggests that regulation of the heart through the sympathetic and parasympathetic (vagal) branches of the autonomic nervous systems is extremely important in maintaining stable rhythms. In particular, it appears that vagal stimulation mitigates the development of ventricular arrhythmias in a variety of experimental studies.

One promissory marker related to SCD is the variability of the heart rate under various conditions. For example, studies using Holter records have shown that low heart rate variability (HRV) is a marker for SCD. Holter studies predominately follow individuals over the course of an average day, mostly reflecting low exercise conditions.

In 1993, a study by van Ravenswaaji et al. reviewed four years of published HRV papers and summarized the various time and frequency domain methods for computation of HRV, which remain largely the same today. This study concluded that HRV is an important surveillance tool for post infarction and diabetic patients to prevent SCD. Although HRV was noted as having a higher association with risk for death than other variables obtained by Holter monitoring, this study also concluded that HRV has a rather low positive predictive value in mass screening (less than 20%). Nonetheless, other studies establish that reduced HRV obtained from 24 hour Holter recordings is an independent predictor of death in chronic heart failure patients.

Another study by Arai et al. analyzed HRV in a cohort of patients undergoing exercise testing and found that the power in the low frequency band [0.03-0.15 Hz] systematically decreased with an increase in exercise and rebounded during recovery after exercise. The low frequency band may be modulated by both the sympathetic and parasympathetic nervous system related to baroreflex activity, temperature regulation and maintenance of homeostasis. The low frequency response to exercise testing was found to be muted in patients with severe congestive heart failure. Conversely, this study found that power in the high frequency band [0.15-0.8 Hz] increased with exercise, decreased through recovery and was highly correlated to respiration—the respiration sinus arrhythmia effect.

Many of the HRV studies have been predicated upon an assumption that a balance between the operation of the parasympathetic (vagal) and sympathetic arms of the autonomic nervous system controls heart rate. For example, as the heart rate increases it has been assumed that sympathetic control increases and vagal influence decreases. Additionally, the low and high frequency bands have been assumed to be related to sympathetic and vagal influence, respectively. Based on these assumptions, the concept of a spectral ratio of these two bands, indicative of this implied balance, was adopted as a potentially useful metric for risk stratification. Because of the low predictive value of the ratio, teachings of Verrier et al. in U.S. Pat. No. 5,437,285 are predicated upon this ratio of low and high frequency components in combination with other metrics for assessing myocardial instability.

Although the concept of a balance between the two components of the autonomic system has been a widely embraced, and presumed to be quantified through a HRV spectral ratio, some studies show that calculations of such a balance of control may not be useful. One study by Eckberg (1997), for example, finds that vagal contributions to baseline low frequency RR-interval fluctuations are great, and evidence that baseline low frequency RR-interval spectral power is related quantitatively to sympathetic-cardiac nerve traffic is nonexistent. This same study concludes that calculations of sympathovagal balance may obscure rather than illuminate human physiology and pathophysiology.

As noted by Kannankeril et al. (2002), risk of SCD is about 17 times higher during or immediately following exercise than at rest. Kannankeril et al. also finds that the vagal influence of heart rate decreases with exercise, and that it appears likely that poor return of vagal control in the post exercise recovery period may be a very critical factor in the progression from instability to fatal arrhythmia.

Although the above described methods for measuring heart rate variability are well known to practitioners of the art and it also is recognized that the patient risk profile may be substantially unveiled during vigorous exercise and recovery, there is no effective method based on HRV for quantifying patient risk from heart rate data collected during exercise and recovery. Therefore, existing methods and apparatus for quantifying risk of SCD based on HRV do not provide an accurate low cost screening tool for mass screening.

SUMMARY

The invention is directed to methods and apparatus that assess the risk of death from cardiovascular causes using information based on variabilities in the heart rate of a patient. Although much progress has been made in using the tools of heart rate variability to characterize records obtained from Holter recording, little work has been done with exercise testing where the effects of the autonomic nervous system are most pronounced. Research has shown that vagal stimulation has a strong anti-arrhythmic effect on the heart, and conversely poor vagal regulation of the heart, particularly during the recovery period following exercise, is a significant risk factor for patients. It is estimated that the risk of SCD is 17-20 times greater during exercise than during the resting phases that dominate Holter recordings, which indicates that the characterization of the risk of cardiovascular death is better unveiled during exercise testing. Several examples of this invention provide new methods and apparatus for (a) characterizing the temporal and spectral characteristics of the variability of the heart rate, and (b) integrating or otherwise using disparate metrics for risk stratification.

One example of a method in accordance with the invention for assessing cardiac risk in a specific patient based on the heart rate variability comprises providing heart activity data of a specific patient including a windowed time series related to heart rate variability during a heart rate test. The windowed time series includes ectopic beats. The method can further include determining a frequency domain value based on either relative energy values of frequency bands or slope of the spectrum across selected frequency ranges of the heart rate variability in the windowed time series, and assessing the risk of a cardiac event based on the frequency domain value.

Another example of a method for assessing cardiac risk in accordance with the invention comprises providing heart activity data of a specific patient including a windowed time series related to heart rate variability during a heart rate test in which the windowed time series includes ectopic beats. This method further includes determining an aggregate power for a frequency band of the windowed time series, and assessing the risk of a cardiac event based on the aggregate power. The aggregate power can be determined by computing a root-means-square value of the windowed time series. In another embodiment, the aggregate power can be determined by performing a Fourier transform of the windowed time series into a spectrum for a frequency domain analysis and then summing the power of the spectral components within a selected frequency band.

Still another method for assessing cardiac risks in a specific patient in accordance with the invention comprises providing heart rate activity including a windowed time series relating to heart rate variability during a heart rate test. This method further includes determining a frequency domain value based on either relative energy values of frequency bands or slope of the spectrum across selected frequency ranges of the heart rate variability in the windowed time series, and determining an aggregate power for a frequency band of the windowed time series. This method further includes assessing the risk of a cardiac event based on the frequency value and the aggregate power.

Apparatus in accordance with the invention can include computers and/or computer operable media containing instructions that cause the computer to receive heart activity data of a specific patient including a windowed time series related to heart rate variability during a heart rate test. The windowed time series can include ectopic beats. The computer also determines (a) a frequency domain value based on either relative energy values of frequency bands or slope of the spectrum across selected frequency ranges of the heart rate variability in the windowed time series, and/or (b) an aggregate power for a frequency band of the windowed time series. In this apparatus, the computer operable medium can further cause the computer to asses the risk of a cardiac event based on the frequency value and/or the aggregate power and output the assessed risk.

BRIEF DESCRIPTION OF THE DRAWINGS

FIG. 4A—patients that remained alive for more than five years after the stress test; and FIG. 4B—patients that died of cardiovascular causes within 5 years of the stress test.

DETAILED DESCRIPTION

The following discussion is presented to enable a person skilled in the art to practice the invention. Various modifications to the disclosed embodiments will be apparent to those skilled in the art, and the generic principles herein may be applied to other embodiments and applications without departing from the spirit and scope of the present invention as defined by the appended claims. Thus, the present invention is not intended to be limited to the embodiments presented, but is to be accorded the widest scope consistent with the principles and features disclosed herein.

A. Overview

Figure 1:
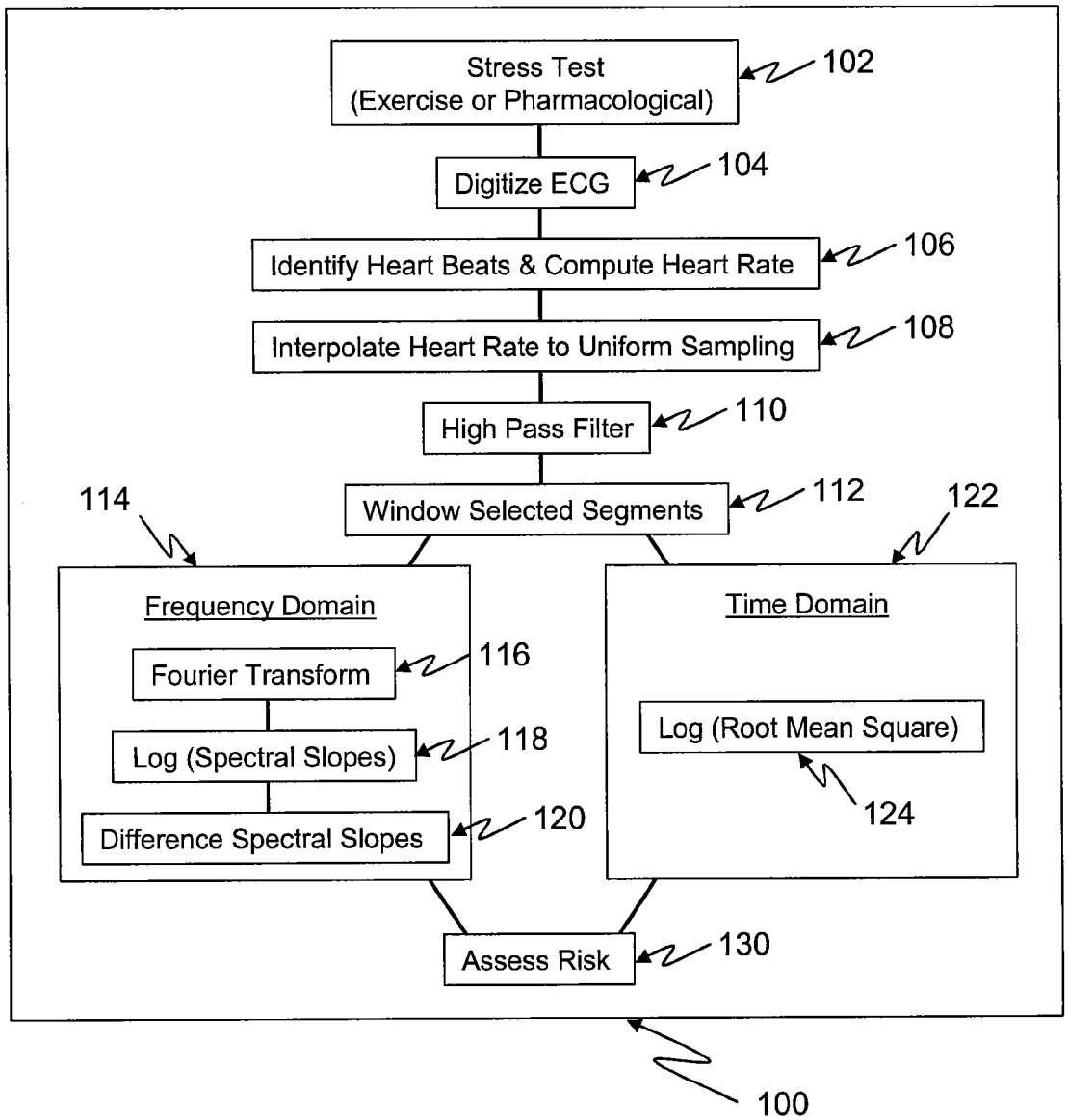
FIG. 1 is a flow chart illustrating a method for determining the risk of cardiovascular death from analysis of heart rate variability in accordance with an embodiment of the invention.

FIG. 1 is a flow chart of a method 100 for quantifying the risk of cardiovascular death using exercise induced heart rate variability metrics. The method 100 includes a stage 102 comprising increasing the heart rate of the patient. This may be accomplished through both exercise and pharmacological protocols. Method 100 continues to a stage 104 comprising digitizing and recording the electrocardiographic (ECG) signals representative of the electrical signal of the beating heart, and a stage 106 comprising analyzing the digitized ECG signal to identify each heart beat. The time of ventricular depolarization is recorded for each beat and the heart rate is computed. The resulting heart rate time series is composed of irregularly spaced heart rate measures, corresponding to the irregular nature of the time between beats. Stage 108 comprises smoothly interpolating this irregular time series into a uniform sampling rate, and stage 110 comprises removing the long period (low frequency) components through high-pass filtering or polynomial based detrending. The high-pass filtered heart rate time series is next analyzed over several time periods corresponding to different phases of the exercise test. This is aided by stage 112 which selects segments of the filtered trace from different times during the test, including both the exercise and recovery phases.

Method 100 includes a frequency domain analysis stage 114 and/or a time domain analysis stage 122 of the heart rate variability. The frequency analysis stage 114 comprises performing a Fourier transform of the windowed trace into the frequency domain (stage 116), determining the slope of the resulting spectrum through a least squares fit to the logarithm of the spectral power (stage 118), and combining the spectral slope from different time windows of the exercise test (stage 120). The time domain analysis in stage 122 comprises computing the logarithm of the square root of the average of the sum of the squares of the windowed trace (log of the root mean square—Log RMS).

Both time domain (RMS) and frequency domain estimates of heart rate variability naturally have different means and standard deviations. These are independent metrics of heart rate variability and either can be used in assessing patient risk. However, it is advantageous to use the two metrics in an integrated estimate of risk. Stage 130 includes methods for assessing patient risk based upon either or both metrics.

B. Stimulating the Heart and Measuring Heart Rate

Stage 102 of method 100 is used to stimulate the heart to beat at a faster rate and is well known in the field of cardiac stress testing. The heart rate can be elevated to maximum capacity via exercise on a treadmill, ergometer, or other exercise devices or through administration of drugs that elevate the heart rate. Cardiac stress tests are typically done using 10 electrodes placed across the chest in order to obtain spatial resolution of distinct aspects of the ECG waveform. However, a single trace measuring the ECG voltage can be used to determine the time of each beat. Time resolution of the heart beats is important and the ECG voltage(s) should be digitized at a diagnostic resolution of 500 or more samples per second in stage 104. Stages 102 and 104 are generally performed in the clinical environment of a cardiac stress test.

Figure 2:
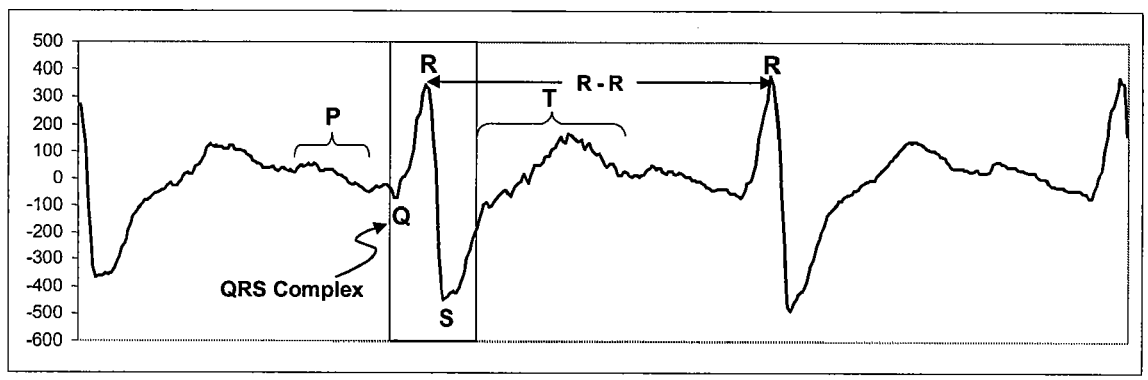
FIG. 2 is a graph illustrating an ECG and the reference points corresponding to activation and recovery of the Atria (P); the ventricle activation phases Q, R and S, forming the QRS complex; the recovery or re-polarization phase T of the ventricles; and the R-R time interval between consecutive beats as measured between the peaks of the R phase.

FIG. 2 illustrates an example ECG with the key phases identified. A normal heart beat starts in the upper chambers of the heart (atria) and the initial ECG phase that records this activation is termed the P-wave portion of the ECG signal. Following the activation of the atria the blood moves into the lower chambers of the heart (ventricles) and activation of the ventricle muscle pumps the blood to the body and generates the ECG phases Q, R and S, often referred to as the QRS complex. Finally, the ventricle muscles recover (repolarize) in anticipation of the next beat, creating the T-wave portion of the ECG signal. Stage 106 can include determining the time interval between adjacent beats to identify the heart beats and compute the heart rate. For example, the time interval between adjacent beats can be measured by measuring the time between the peaks of the R wave (the R-R interval). A more robust measure of R-R intervals, particularly when the peak of the R wave is not sharp, can be obtained by cross-correlating the QRS complex from an average or median beat with each subsequent beat and noting the time of maximum correlation. Stage 106 can be performed using either approach to determining R-R intervals.

Figure 3:
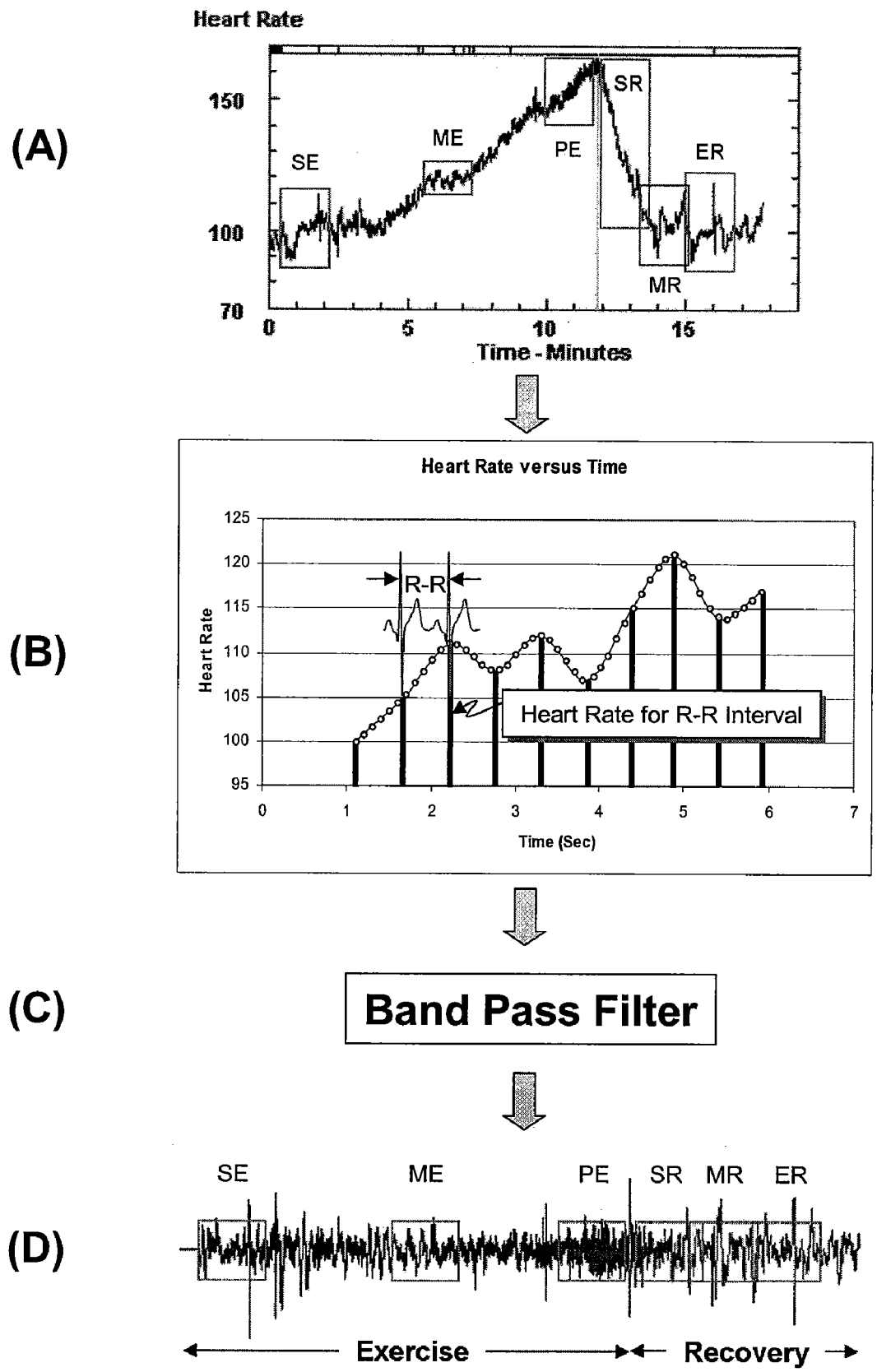
FIG. 3 is a flow chart illustrating the processing stages starting with a raw instantaneous heart rate determined over the course of an exercise stress test (A), through a resampling to a uniform time basis (B), followed by selected band pass filtering or detrending (C), resulting in a final time series for heart rate variability analysis (D).

For every beat detected the instantaneous heart rate, measured in beats per minute, for HRV analysis is computed from the R-R interval between the current and proceeding beats by the simple equation $HR=60/(R-R)$, where the R-R interval is measured in seconds. FIG. 3A is an example of a graphical representation of the output of stage 106 showing a typical plot of continuous heart rate during a stress test. In this example, the heart rate starts at time 0 at about 90 beat/sec and remains low during the start of exercise (SE), increases throughout the middle exercise period (ME) until it climbs to a peak of over 160 beat/sec at peak exercise (PE), and then rapidly declines during the start of recovery (SR) as the patient recovers until it returns to the low range at the end of recovery (ER).

C. Signal Conditioning and Windowing

Because the beats occur irregularly in time, the resulting instantaneous heart rate time series is not uniformly sampled. As most signal processing techniques are more efficient when the series is uniformly sampled, stage 108 is useful because it interpolates or transforms the heart rate data onto a uniformly sampled series. FIG. 3B is an example of a graphical representation illustrating the process of stage 108. The vertical bars represent the location in time of the R wave from each beat and the height of each bar represents the instantaneous heart rate computed from the R-R interval between one beat and its proceeding beat. In one example, stage 108 includes using a cubic spline under tension curve to interpolate the instantaneous heart rate sequence to a uniformly sampled time series represented by the small circles on the smooth curve. Although the interpolated sample rate is not critical, it should be above the Nyquest frequency corresponding to the highest heart rate or above the shortest R-R interval in the data. For example, a sampling rate of 10 samples/sec is expected to be sufficient and convenient. The time series for HRV analysis can be computed from either the measured heart rates or from the measured R-R intervals. When using R-R intervals for HRV, the vertical bars in FIG. 3B represent the R-R interval time instead of the reciprocal metric heart rate.

Traditional HRV analysis focuses on R-R intervals between normal beats, where "normal" is the dominant beat in the series. Ectopic beats and the adjacent R-R intervals are excluded from the irregular time series and any subsequent interpolated series and analysis in traditional HRV analysis. However, ectopy may introduce feedback to heart rate through the baroreceptor mechanisms that may last as long as approximately 10 seconds. Conventional HRV analyses that merely remove ectopic beats accordingly remove the stimulus while leaving the response. This can vitiate the value of the spectral analysis. Furthermore, some methods that remove ectopy effectively time-shift the subsequent beat pattern by the missing intervals, which can destroy the phase information and alter the spectral amplitude information in unpredictable ways. Although it may be ideal to have perfect records without ectopy, methods in accordance with many examples of the present invention include the ectopic beats and the fidelity of the temporal position and response of the subsequent beats. This accordingly avoids the downfalls of excluding such data.

Stage 110 compensates for such irregularities so that the data can include ectopic beats. In many examples, stage 110 includes reducing the heart rate data via filtering the heart rate time series over selected periods, such as at peak exercise (PE) and start of recover (SR), using a selected band filter. The filtered heart rate time series can contain very long signal periods representing the progression of the heart rate to a peak value at the limits of physical exercise (PE) and a rapid return to baseline as the patient recovers (SR). The shorter frequencies of the heart rate intervals are of principal interest for HRV analysis, and thus a high-pass filter can be used to select shorter frequencies for the windowed time series. A single or multi-pole infinite or finite impulse response filter may be used in effecting the filtering. A two-pole Butterworth high-pass filter with a corner at 0.015 Hz has been found to be effective.

The heart rate signal does not reflect a stationary process. The time series around peak exercise (PE) is particularly important for the HRV analysis, and a filter that extended the filter impulse response from the exercise phase into the sharply contrasting recovery phase would distort the true frequency characteristics of the recovery phase. As the amplitude characteristics are important in the spectral analysis, and the phase information less significant, it is useful to apply the high pass filter in a forward direction from the start of the time series to peak exercise (PE) and in a reverse direction from the end of the record to the same sample at the peak. FIG. 3D is an example of a graphical representation showing the two segments representing filtered exercise and recovery joined for display purposes, but HRV analysis should not extend over this discontinuity. This procedure isolates the distinct non-stationary aspects of the exercise and recovery phase of the test and preserves the temporal amplitude information in the heart rate data.

Stage 112 includes setting a window for segments of the filtered heart rate time series. Any segment of the filtered time series may be used for HRV analysis for stage 112. However, a representative characterization of the changing HRV signal can be obtained through analysis of six segments corresponding to the start (SE), middle (ME) and peak (PE) of exercise, and the start (SR), middle (MR) and end (ER) of recovery shown by the boxed areas in FIGS. 3A and 3D. The window length of the boxed areas can be adjusted depending upon several considerations. For spectral analysis, it is desirable to choose window lengths that are powers of 2 (e.g.: 512, 1024, etc). Because the longest periods of interest are around 25 seconds, corresponding to a frequency of 0.04 Hz, it is generally useful to extend the window to a length of one or more multiples of the longest periods of interest. Conversely, temporal resolution of vagal changes is diminished as the window length extends. In practice a window length of 102.4 seconds, corresponding to 1024 samples, has proven effective.

Alternatively, the procedure for reducing the heart rate data in stage 110 can include detrending via fitting a low-order polynomial curve to the heart rate data over the selected window segment and subtracting the resulting curve from the heart rate data. This alternative reducing procedure via detrending the heart rate data may be employed using either the raw heart rate beat data (results from stage 106), or the uniformly interpolated data from stage 108. In practice, a second order polynomial has been found to do an excellent job of detrending stress test heart rate data over a window length of 102.4 seconds, but in still additional embodiments of the invention higher or lower order polynomials may be used to detrend stress test heart rate data over other window lengths.

D. Frequency Domain Analysis (Stage 114)

The windowed time series from method 112 are multiplied by a Hanning window and Fourier transformed using standard methods familiar to those skilled in the art of signal processing, method 116. Several specific frequency bands are described below to provide examples of useful frequencies, but other frequencies may be used. The frequency domain analysis provides a frequency value that can be used to assess the risk of SCD. One unique finding of the present invention is that the spectral slopes of the average power in various spectrums is a diagnostic of risk stratification for CV death.

Although the resulting spectrum can be analyzed as a whole, distinctly different physical processes have been found to correlate with distinct frequency bands in the signal (see van Ravenswaaji et al., 1993). The high frequency spectral band [0.4-1.0 Hz] has been found to capture the respiration induced HRV. At the low frequency end, the spectral band [0.04-0.15 Hz] has been found to be modulated by both the sympathetic and parasympathetic nervous system related to baroreflex activity, temperature regulation and maintenance of homeostasis. The remaining middle band [0.15-0.4 Hz] provides a transition between the low and high bands. The power in each band, in decibels (db), can be computed by integrating the logarithm of the spectrum over the defined frequency range of each band, method 118.

Figure 4:
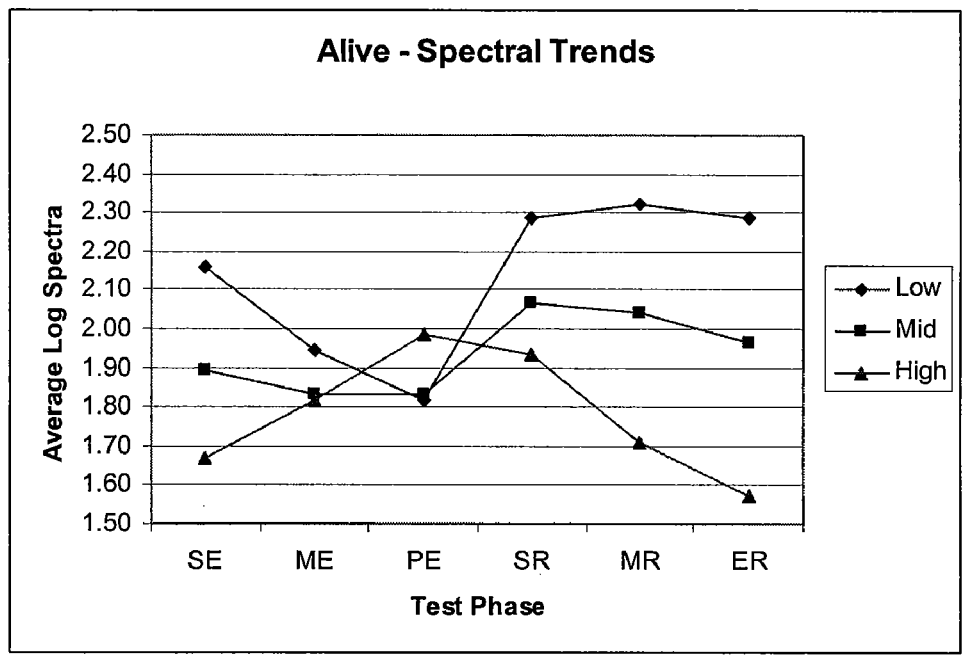
FIGS. 4A and 4B illustrate two examples of the spectral trends for three frequency bands (low, mid and high) over the course of the exercise test for two populations.
Figure 4:
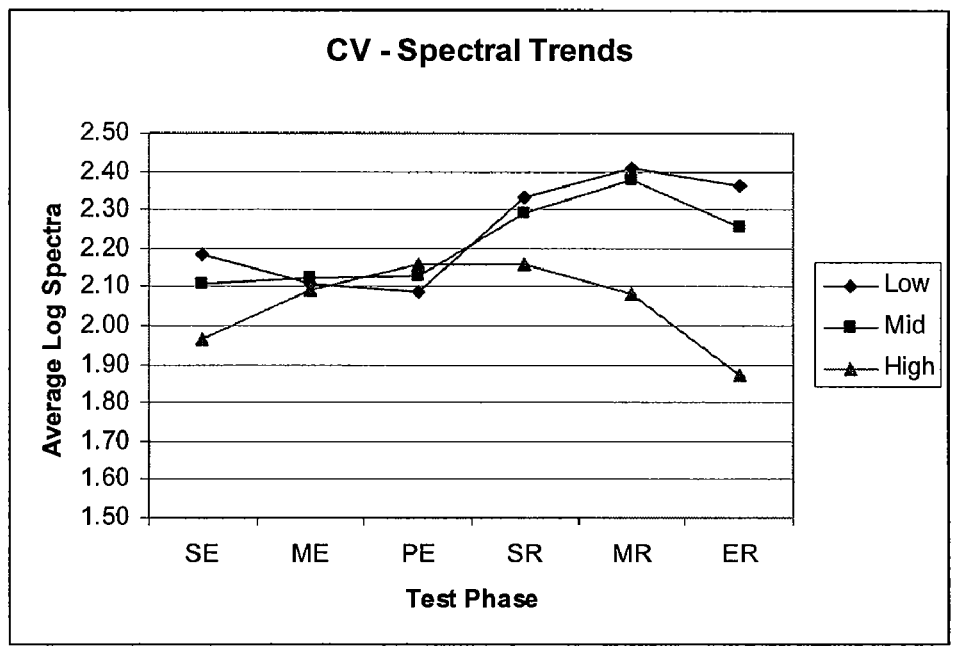

FIG. 4A shows the average power for the three spectral bands for the six windowed phases of the exercise test from 1,783 patients, from a total cohort of 1,959 patients, that were still alive after a 5 year follow-up period. The high frequency band shows a progressive increase to peak exercise, corresponding to increasing respiration induced sinus arrhythmia, that decays over the course of recovery. Conversely, the longer period bands show a distinct decay in HRV power as exercise progresses, reaching a minimum at peak exercise and rebounding dramatically in recovery. The first analysis in recovery (SR) for the low frequency band, corresponding to the first 102.4 sec of recovery, is characterized by HRV power greater than that recorded at the initial stage of exercise (SE). The mid-band follows the low band, but somewhat muted in overall response. This signal shape is interpreted to represent the process of reduced vagal mediation of heart rate and heart rate variability as exercise progresses, followed by a very rapid return of vagal control in the early stage of recover.

FIG. 4B shows a similar plot, but for the average power from of 55 patients, from the cohort of 1,959 patients, that died of cardiovascular (CV) causes over the following 5 year period. It is important to note the muted overall spectral response of these patients relative to the spectra in FIG. 4A.

Figure 5:
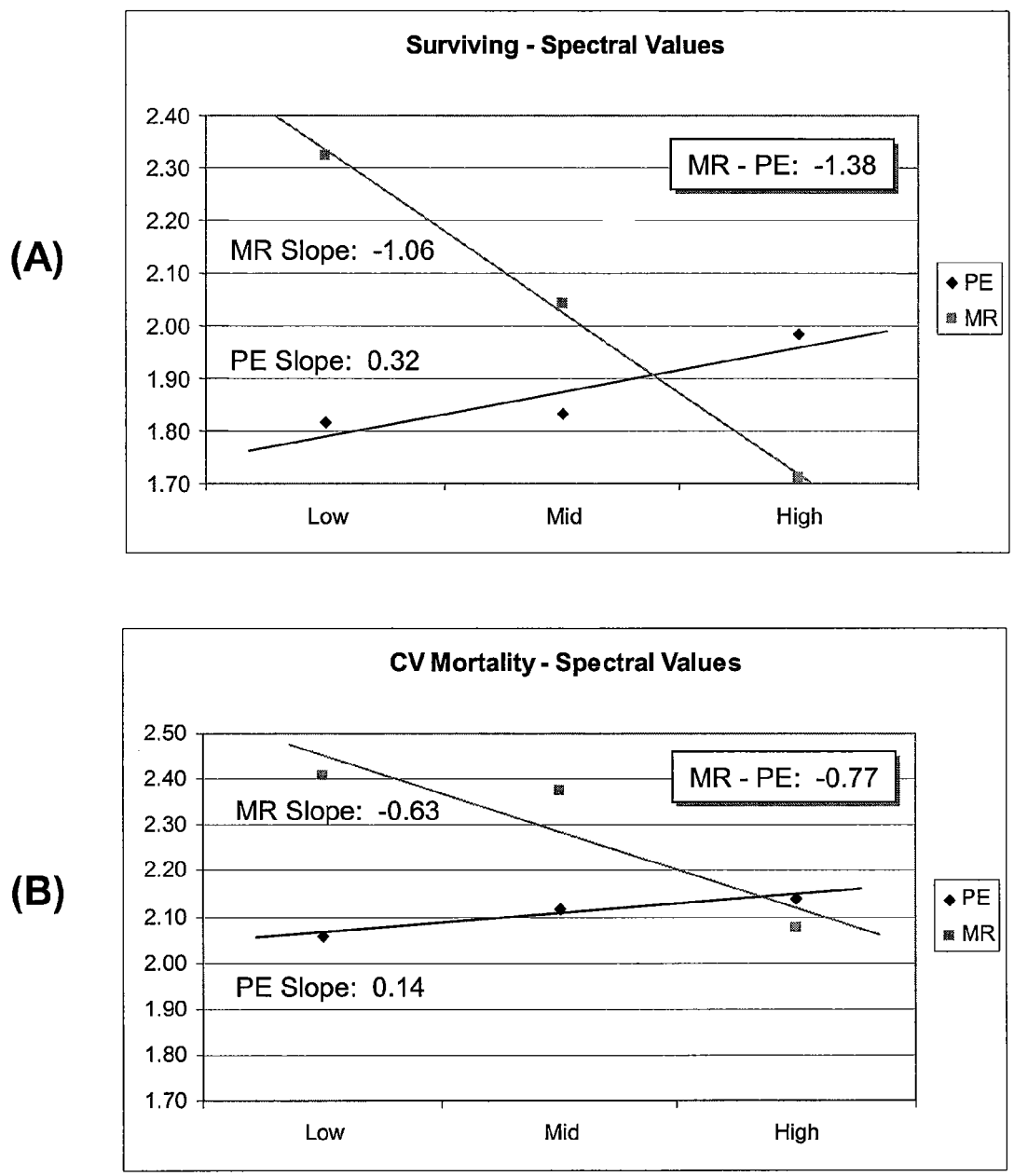
FIGS. 5A and 5B illustrate the spectral slopes associated with peak exercise and mid recovery for a surviving cohort (FIG. 5A) and a CV mortality cohort (FIG. 5B).
FIG. 5C illustrates two example spectra and an alternative method for determining spectral slope across a selected frequency band.
Figure 5:
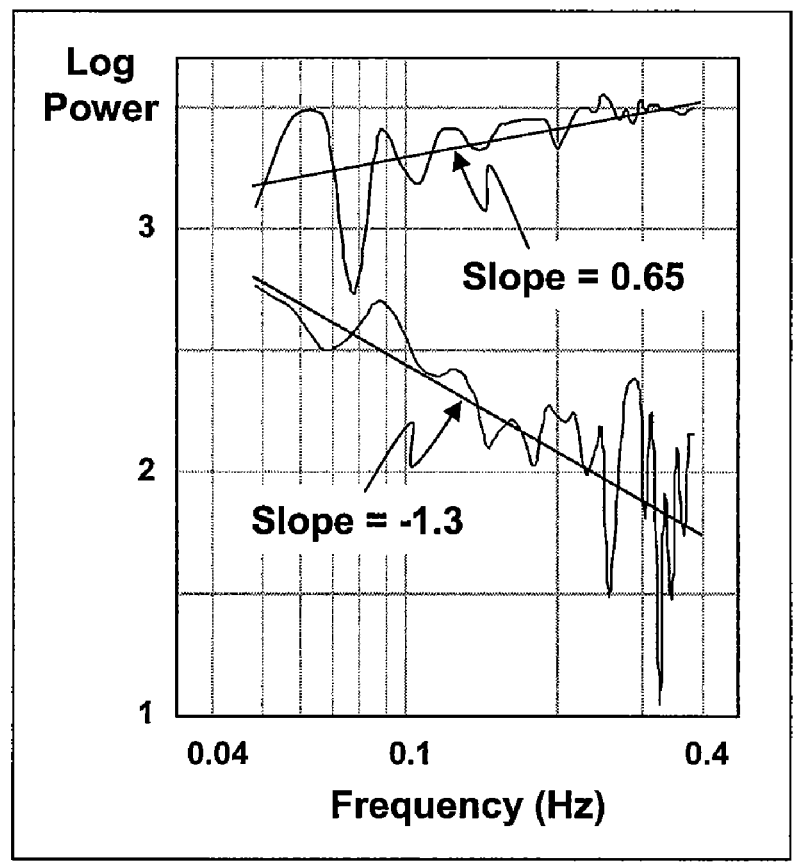

The spectral differences between the alive population (FIG. 4A) and those dying of CV causes (FIG. 4B) can be quantified in several ways. For instance, at the start of exercise the low frequency band shows significant augmentation, relative to the mid or high bands. The difference in separation between the low and high bands is much reduced in the CV population. At peak exercise this relationship is reversed, with the high band containing more energy than the lower bands for both populations but again muted in the CV population. The recovery phase is characterized by a rebound of the low band and a falling-off of the high band, but again muted for the CV population. These trends are readily apparent when the spectrum is examined relative to different points in the exercise test. FIG. 5 shows the power in the spectral bands for peak exercise and mid recovery; the slope of the line fit to the three points across the bands, for each time interval, provides an effective characterization of the changing spectral throughout the test. The slope difference between peak exercise and other times has proven to provide an effective metric for risk stratification. The prognostic optimal difference has been found to occur between mid recovery and peak exercise: Slope(MR)−Slope(PE), method 122.

It is important to note that the slope can be calculated via several methods. In FIGS. 5A and B the slope is computed via a least squares fit of a line to the average power in the three spectral bands. This is effectively the fit of a line in Log (power) and Log (frequency) space. Conversely a line could be fit to the raw spectrum across a broader frequency range, for instance 0.04-1.0 Hz. Another method would include dividing the spectra from the two time intervals before taking the logarithm of the power and fitting the line to the resulting log(spectra).

FIG. 5C illustrates an alternative procedure for spectral slope heart rate variability analysis by fitting a line to the Log (power) versus Log (frequency) over a selected frequency range. Spectral slope estimates from different time windows of the stress test may also be combined to improve signal to noise. In one example of this alternative procedure, the average of the spectral slope estimates over the frequency range 0.04-0.4 Hz, for the time intervals of mid-exercise and start recovery, has proven to provide an effective prognostic score for risk stratification for CV death. As ectopy tends to introduce high frequency energy into the heart rate variability spectrum, lowering the highest frequency used in analysis from 1 Hz to 0.4 Hz tends to lower the potential noise associated with ectopy.

E. Time Domain Analysis (Stage 116)

Figure 6:
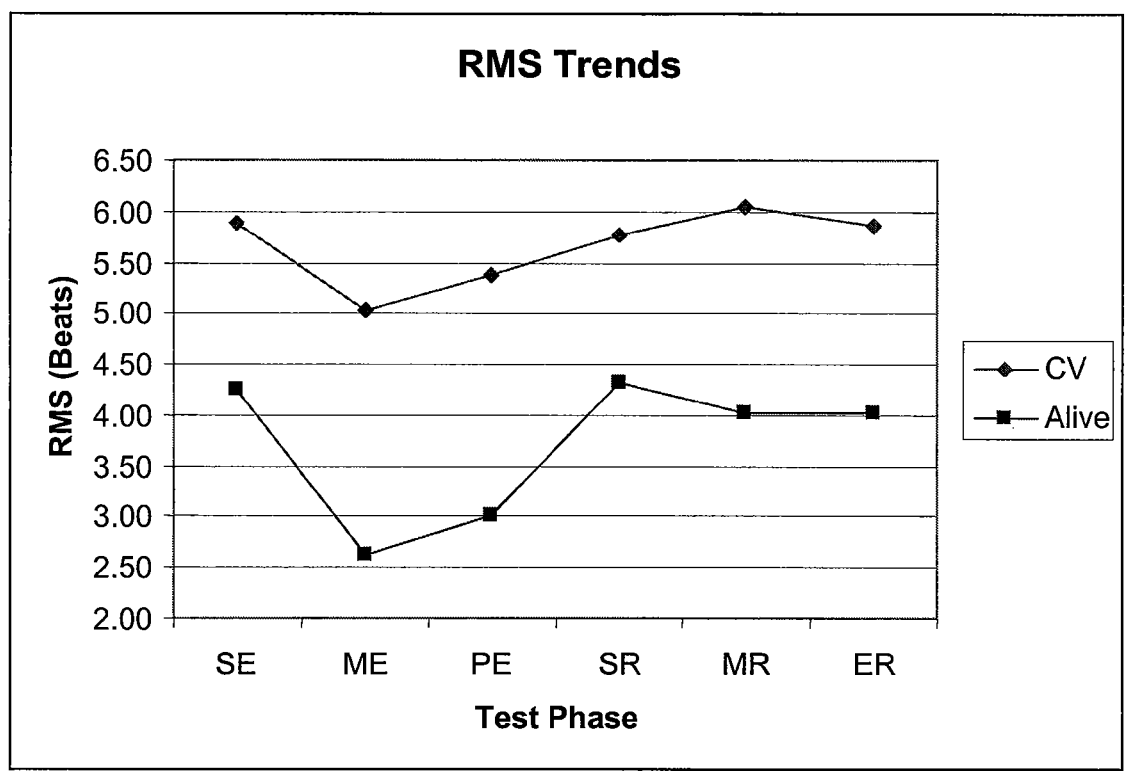
FIG. 6 illustrates the root mean square (RMS) amplitude, in beats/minute, of the processed heart rate time series for both the alive and CV cohorts throughout the exercise test.

In examining FIGS. 4A and 4B it is also apparent that the aggregate power, or level, in the alive population is lower than for the CV population. For instance, the spectral value for the low frequency band for the alive population is about 1.85 and nearly 2.1 for the CV population. There is no a priori or physical reason why the shape of the spectral trends should be tied to the absolute level of the power (e.g., the aggregate power), and another unique finding of the present invention is that the power level is diagnostic for risk stratification for CV death. The total or aggregate power contained in the spectrum for any time windowed data can be obtained by integrating the power over the entire spectrum. Conversely, as noted by Parseval in 1799, the power contained in the spectrum is exactly equivalent to the square root of the sum of the squares (RMS) of the original time series, a simple variant in the fundamental principle of equivalent energy in either the time or frequency representation. The RMS computation of spectral power for each windowed and high pass filtered or detrended series is a low cost method to execute and has proven useful for risk stratification, method 124. FIG. 6 shows the RMS values (in units of beats/min) for the alive and CV death patients in the studied cohort for all six windows of the exercise test. Note that the RMS value for the alive patients is systematically below the CV death patients; the difference at peak exercise has been found to be most prognostic.

For statistical analysis, the windowed time series has a zero mean value as a necessary result of the high-pass filtering and the RMS values will not be normally distributed due to the hard limit of zero on the low side of the RMS distribution. Following the use of decibels (log of the spectrum) for the spectral estimates, it is statistically useful to use the log of the RMS for analysis, which transforms this energy metric into a more normal distribution.

F. Risk Assessment

The frequency value based on the spectral slope (HRV Slope) and the aggregate power based on the RMS computation provide estimates of HRV that are both highly predictive of CV death in the cohort discussed above and portrayed in FIGS. 4A and 4B. The correlation coefficient between these two parameters, for this large cohort, is relatively low (r=0.2), indicating they are independent. To improve risk stratification it is useful to combine these parameters into a single unified metric, method 130.

Figure 7:
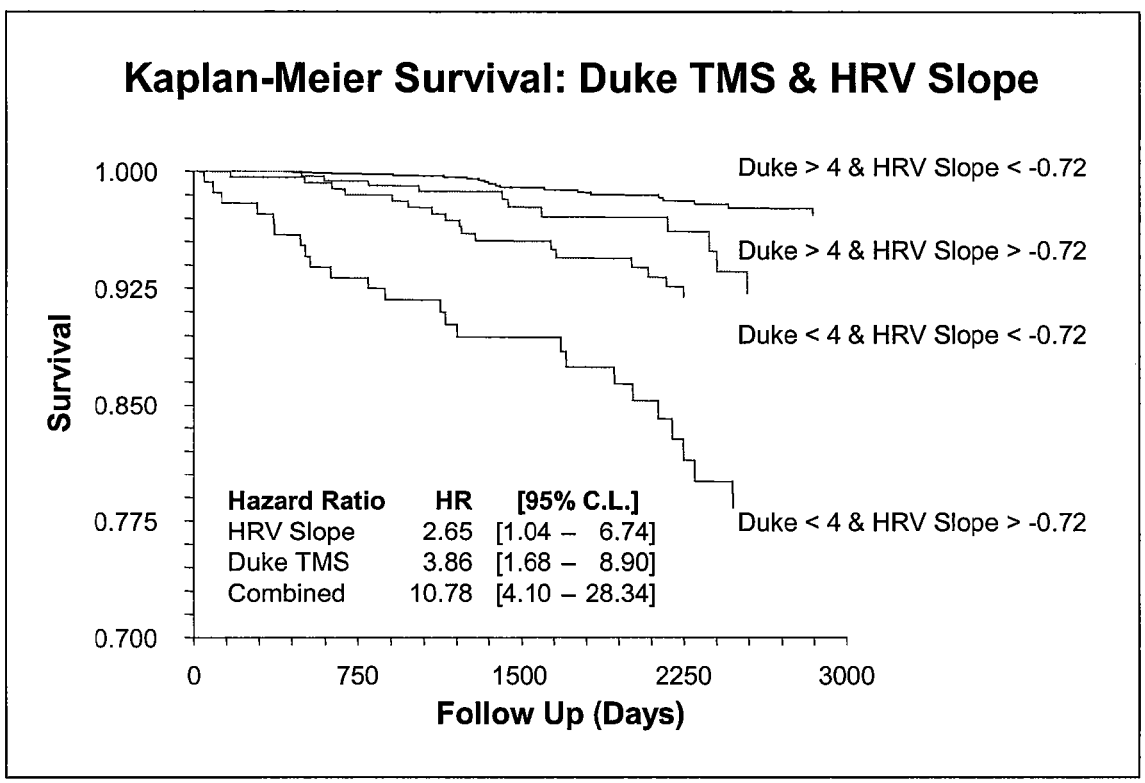
FIG. 7 illustrates the Kaplin-Meier assessment of survival for patients with abnormal values for the Duke Treadmill Score and for the HRV slope (MR-PE) metrics.

Risk assessment methodologies using Cox proportional hazard and Kaplan-Meier survival analysis are well known to those familiar with prognostic statistical analysis in the medical industry. The HRV Slope and the aggregate power parameters discussed in methods 114 and 122 have been assessed relative to the existing Duke Treadmill Score (TMS), the current industry "gold" standard exercise based prognostic metric for risk stratification. FIG. 7 shows the survival analysis for the four combinations of normal and abnormal measures for the Duke TMS and HRV Slope metric. An abnormal HRV Slope metric increases a patient's risk of CV death by ~2.6 times over a normal score. An abnormal Duke TMS score increases a patients risk to ~3.9 times greater than normal. A Cox proportional hazard analysis shows that the Duke TMS metric is an independent parameter, distinct from HRV Slope, and the combined Kaplan-Meier hazard ratio when both metrics are abnormal is ~10.8 times greater, a significant increase in risk over the estimate based upon the current gold standard Duke TMS.

Figure 8:
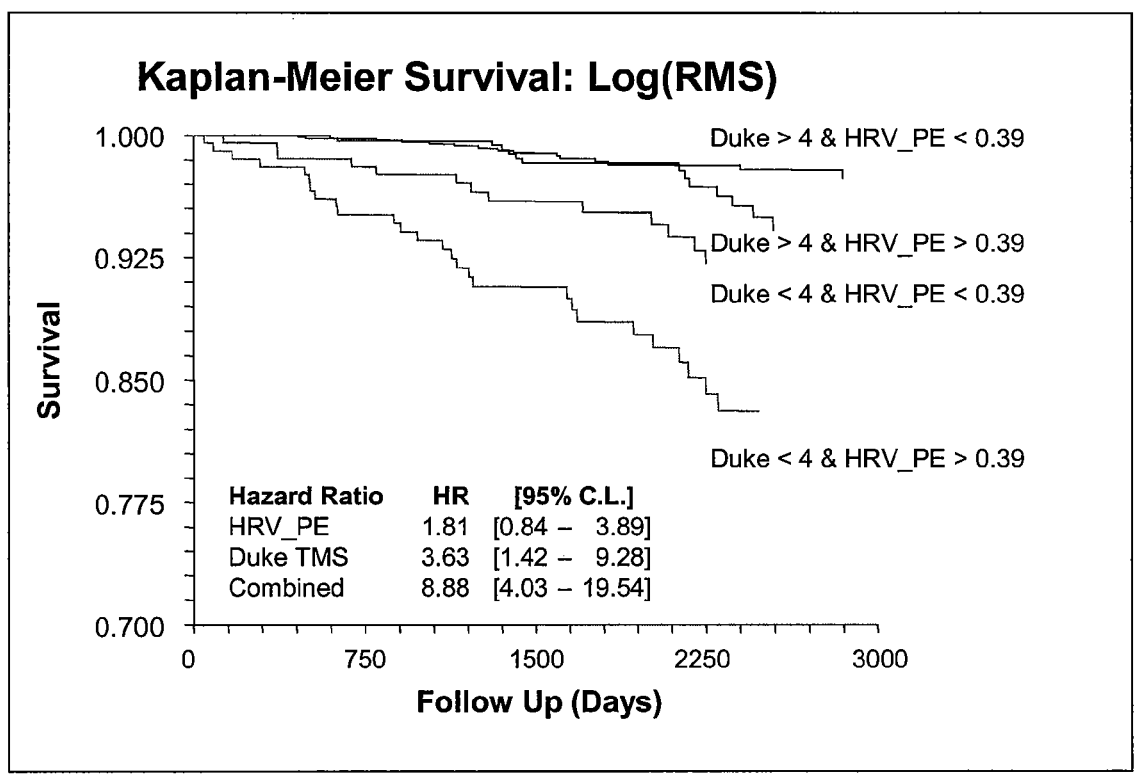
FIG. 8 illustrates the Kaplin-Meier assessment of survival for patients with abnormal values for the Duke Treadmill Score and for the HRV RMS metrics.

FIG. 8 shows a similar analysis for HRV aggregate power at peak exercise combined again with the Duke TMS for comparison. The HRV aggregate power metric is independent of the Duke TMS and the HRV Slope metrics. HRV aggregate power metric increases a patient's risk of CV death by ~1.8 times over a normal score. In this combination, an abnormal Duke TMS score increases a patients risk to ~3.6 times greater than normal. The combined Kaplan-Meier hazard ratio when both metrics are abnormal is ~8.9 times greater, a significant increase in risk over the estimate based upon either parameter alone.

Figure 9:
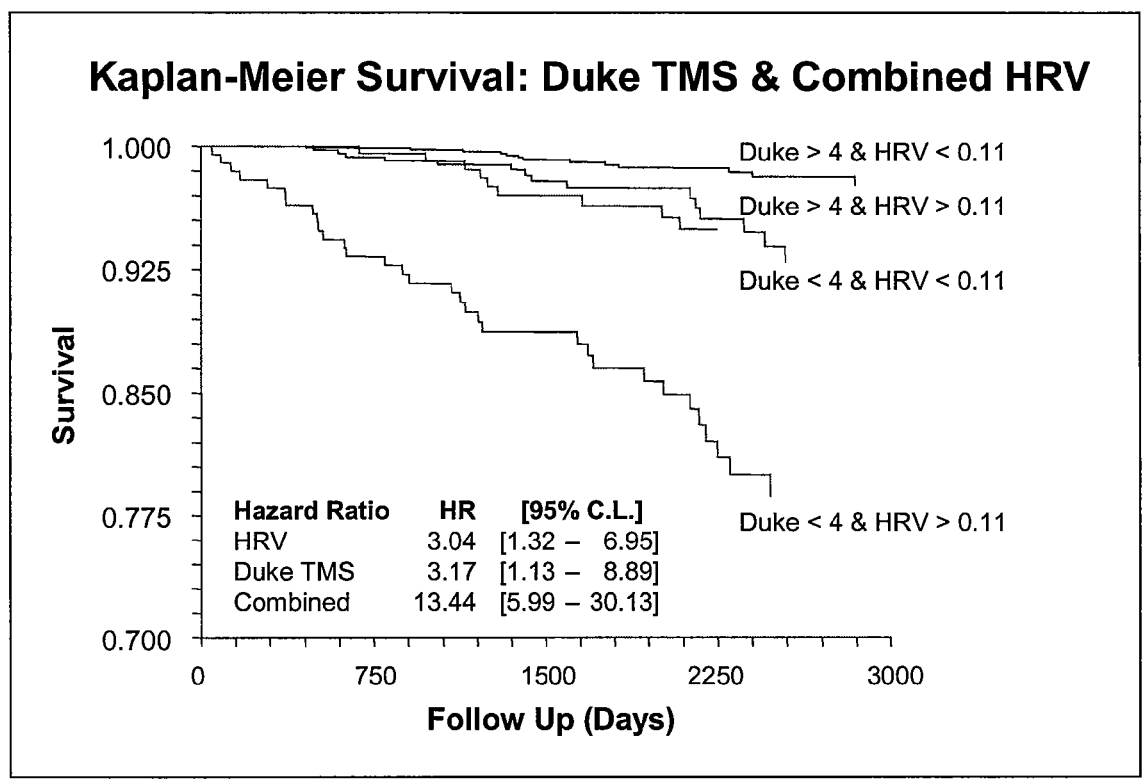
FIG. 9 illustrates the Kaplin-Meier assessment of survival for patients with abnormal values for the Duke Treadmill Score in both the HRV Slope (MR-PE) and HRV RMS metrics.

Finally, the combination of the two HRV metrics, along with the Duke TMS is shown in FIG. 9. An abnormal score in both HRV Slope and the aggregate power increases a patient's risk of CV death ~3 times greater than normal, compared with an increase in risk to ~3.2 when just the Duke TMS is abnormal. When both HRV metrics and the Duke TMS metric are all abnormal, the risk of CV death increases to ~13.4—a very dramatic increase over the current gold standard Duke TMS. As such, the new HRV metrics are complimentary to the Duke TMS and provide a significant improvement in risk assessment when used together.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

I claim:

1. A method for assessing cardiac risks in a specific patient based on heart rate variability, comprising:
providing heart activity data of a specific patient including a windowed time series related to heart rate variability during a heart rate test;
determining a frequency domain value based on at least one of energy values of frequency bands and spectral slope(s) across selected frequency ranges of the heart activity data in the windowed time series; and
assessing the risk of a cardiac event based on the frequency domain value;
wherein providing heart activity data comprises determining an instantaneous heart rate sequence from an ECG waveform obtained during an exercise period of increasing heart rate and a recovery period of decreasing heart rate, providing a uniform sample series of the instantaneous heart rate sequence, and reducing the uniform sample series by filtering and/or detrending via fitting a polynomial function to the heart activity data across a selected time window to obtain a heart rate variability waveform associated with variances in the heart rate between beats in a desired frequency band.

2. The method of claim 1 wherein: determining an instantaneous heart rate sequence comprises ascertaining R-R intervals of the ECG waveform; and reducing the uniform sample series comprises at least one of processing the uniform sample series through a high-pass filter and detrending by subtraction of a fit polynomial function to the heart activity data that provides the heart rate variability waveform for shorter frequencies.

3. The method of claim 1 wherein: determining an instantaneous heart rate sequence comprises ascertaining R-R intervals of the ECG waveform and expressing the instantaneous heart rate sequence in beats/minute; providing a uniform sample series of the instantaneous heart rate sequence comprises interpolating between adjacent beats at a uniform sample rate; and reducing the uniform sample series comprises at least one of processing the uniform sample series through a high-pass filter and detrending by subtraction of a fit polynomial function to the heart activity data that provides the heart rate variability waveform for shorter frequencies.

4. The method of claim 1 wherein reducing the uniform sample series comprise filtering in the forward direction through at least a portion of the exercise period of the heart rate test to approximately an end of a peak exercise phase and reverse filtering through at least a portion of the recovery period to approximately the end of the peak exercise phase.

5. The method of claim 1 wherein detrending comprises fitting a polynomial function to the heart activity data either before or after interpolation for the windowed time series and subtracting the resulting function from the heart activity data.

6. The method of claim 1, further comprising performing a Fourier transform of the windowed time series into a spectrum for frequency domain analysis.

7. A method for assessing cardiac risks in a specific patient based on heart rate variability, comprising:
   providing heart activity data of a specific patient including a windowed time series related to heart rate variability during a heart rate test;
   determining a frequency domain value based on at least one of energy values of frequency bands and spectral slope(s) across selected frequency ranges of the heart activity data in the windowed time series; and
assessing the risk of a cardiac event based on the frequency domain value;
   wherein determining a frequency domain value based on at least one of the energy values comprises (a) fitting a line to the spectral power across a selected frequency range, and (b) determining a slope of the line to obtain a spectral slope, wherein the frequency domain value comprises the spectral slope.

8. A method for assessing cardiac risks in a specific patient based on heart rate variability, comprising:
   providing heart activity data of a specific patient including a windowed time series related to heart rate variability during a heart rate test;
   determining a frequency domain value based on at least one of energy values of frequency bands and spectral slope(s) across selected frequency ranges of the heart activity data in the windowed time series; and
   assessing the risk of a cardiac event based on the frequency domain value;
   wherein assessing the risk of a cardiac event comprises comparing the determined frequency domain value with a reference frequency domain value range associated with a population that has experienced the cardiac event.

9. The method of claim 8 wherein providing the heart activity data comprises: identifying a peak exercise phase and a mid-recovery phase of the heart rate test; determining instantaneous heart rate sequences for the peak exercise phase and the mid-recovery phase by ascertaining R-R intervals of an ECG waveform of the peak exercise phase and the mid-recovery phase; providing uniform sample series of the instantaneous heart rate sequences by interpolating between adjacent beats at a uniform sample rate; and filtering the uniform sample series by high-pass filtering the uniform sample series in a forward direction through at least a portion of the exercise period and reverse filtering through at least a portion of the recovery period to provide the heart rate variability waveform for shorter frequencies during the peak exercise phase and the mid-recovery phase.

10. The method of claim 9 wherein: for the peak exercise phase, the energy values comprise a peak exercise low frequency average power, a peak exercise middle frequency average power, and a peak exercise high frequency average power of the windowed time series, and wherein determining the frequency domain value comprises determining a peak exercise frequency domain value by (a) fitting a peak exercise line to the peak exercise low frequency average power, the peak exercise middle frequency average power, and peak exercise the high frequency average power, and (b) determining a slope of the peak exercise line to obtain a peak exercise spectral slope, wherein the peak exercise frequency domain value comprises the peak exercise spectral slope; and for the mid-recovery phase, the energy values further comprise a mid-recovery low frequency average power, a mid-recovery middle frequency average power, and a mid-recovery high frequency average power of the windowed time series, and wherein the method further comprises determining a mid-recovery frequency domain value by (a) fitting a mid-recovery line to the mid-recovery low frequency average power, the mid-recovery middle frequency average power, and the mid-recovery high frequency average power, and (b) determining a slope of the mid-recovery line to obtain a mid-recovery spectral slope, wherein the mid-recovery frequency domain value comprises the mid-recovery spectral slope.

11. The method of claim 8 wherein: for the peak exercise phase, the energy values comprise a peak exercise low frequency average power, a peak exercise middle frequency average power, and a peak exercise high frequency average power of the windowed time series, and wherein determining the frequency domain value comprises determining a peak exercise frequency domain value by (a) fitting a peak exercise line to the peak exercise low frequency average power, the peak exercise middle frequency average power, and peak exercise the high frequency average power, and (b) determining a slope of the peak exercise line to obtain a peak exercise spectral slope, wherein the peak exercise frequency domain value comprises the peak exercise spectral slope; and for the mid-recovery phase, the energy values further comprise a mid-recovery low frequency average power, a mid-recovery middle frequency average power, and a mid-recovery high frequency average power of the windowed time series, and wherein the method further comprises determining a mid-recovery frequency domain value by (a) fitting a mid-recovery line to the mid-recovery low frequency average power, the mid-recovery middle frequency average power, and the mid-recovery high frequency average power, and (b) determining a slope of the mid-recovery line to obtain a mid-recovery spectral slope, wherein the mid-recovery frequency domain value comprises the mid-recovery spectral slope, and the method further comprises fitting a line across selected frequency ranges for mid-exercise phase and for the start recovery phase, and combining the two determined slopes.

12. The method of claim 11 wherein combining the two determined slopes comprises subtracting the slopes.

13. The method of claim 11 wherein combining the two determined slopes comprises averaging the slopes.

14. The method of claim 11 wherein assessing the risk of a cardiac event comprises at least one of (a) comparing a difference between the determined peak exercise frequency domain value and the determined mid-recovery exercise frequency value with a difference between a reference peak exercise frequency domain value associated with a population that has experienced the cardiac event and a reference mid-recovery frequency domain value associated with the population that has experienced the cardiac event, and (b) fitting a line to the Log (power) versus Log (frequency) over a selected frequency range, determining spectral slope estimates from different time windows of the stress test, and combining the spectral slope estimates to provide a good signal to noise ratio.

15. A method for assessing cardiac risks in a specific patent based on heart rate variability, comprising:
  providing heart activity data of a specific patient including a windowed time series related to heart rate variability during a heart rate test, the windowed time series including ecotopic beats;
  determining an aggregate power for a frequency band of the windowed time series; and
  assessing the risk of a cardiac event based on the aggregate power;
  wherein providing heart activity data comprises determining an instantaneous heart rate sequence from an ECG waveform obtained during an exercise period of increasing heart rate and a recovery period of decreasing heart rate, providing a uniform sample series of the instantaneous heart rate sequence, and reducing the uniform sample series via filtering the heart activity data and/or detrending by subtraction of a fit polynomial function of the heart rate variability data to obtain a heart rate variability waveform associated with variances in the heart rate between beats in a desired frequency band; and
  determining the aggregate power comprise performing (a) a Fourier transform of the windowed time series into a spectrum for frequency domain analysis and/or (b) a root-means-square computation of the filtered or detrended time series.

16. The method of claim 15 wherein: determining an instantaneous heart rate sequence comprises ascertaining R-R intervals of the ECG waveform; reducing the uniform sample series comprises at least one of processing the uniform sample series through a selected band filter and detrending by subtraction of a fit polynomial function of the heart rate variability data that provides the heart rate variability waveform for selected frequencies; and expressing the instantaneous heart rate sequence in beats/minute.

17. The method of claim 16 wherein: determining an instantaneous heart rate sequence comprises ascertaining R-R intervals of the ECG waveform; providing a uniform sample series of the instantaneous heart rate sequence comprises interpolating between adjacent beats at a uniform sample rate; and reducing the uniform sample series comprises at least one of processing the uniform sample series through a selected band filter and detrending by subtraction of a fit polynomial function of the heart rate variability data that provides the heart rate variability waveform for selected frequencies.

18. A method for assessing cardiac risks in a specific patent based on heart rate variability, comprising:
  providing heart activity data of a specific patient including a windowed time series related to heart rate variability during a heart rate test, the windowed time series including ecotopic beats;
  determining an aggregate power for a frequency band of the windowed time series; and
  assessing the risk of a cardiac event based on the aggregate power;
  wherein providing the heart activity data comprises: identifying a peak exercise phase and a mid-recovery phase of the heart rate test; determining instantaneous heart rate sequences for the peak exercise phase and the mid-recovery phase by ascertaining R-R intervals of an ECG waveform of the peak exercise phase and the mid-recovery phase; providing uniform sample series of the instantaneous heart rate sequences by interpolating between adjacent beats at a uniform sample rate; reducing the uniform sample series comprises filtering the uniform sample series through a selected band filter in a forward direction through at least a portion of the exercise period and a reverse direction through at least a portion of the recovery period to provide the heart rate variability waveform for a selected frequency band during the peak exercise phase and the mid-recovery phase, and/or determining an average of slopes of the mid-exercise and start-recovery phases.

19. The method of claim 18 wherein the aggregate power comprises a sum of the power of the spectral components within the selected frequency band.

20. A method for assessing cardiac risks in a specific patent based on heart rate variability, comprising:
  providing heart activity data of a specific patient including a windowed time series related to heart rate variability during a heart rate test, the windowed time series including ecotopic beats;
  determining an aggregate power for a frequency band of the windowed time series; and
  assessing the risk of a cardiac event based on the aggregate power;
  wherein determining an aggregate power comprises performing a root-means-squared computation of corresponding filtered time series.

21. The method of claim 20 wherein assessing the risk of a cardiac event comprises comparing the determined aggregate power with a reference aggregate power range associated with a population that has experienced the cardiac event.

22. The method of claim 20 wherein assessing the risk of a cardiac event comprises comparing corresponding aggregate powers for the peak exercise low frequency, peak exercise middle frequency, peak exercise high frequency, mid-recovery low frequency, mid-recovery middle frequency, and mid-recovery high frequency with corresponding reference aggregate powers associated with a population that has experienced the cardiac event.

23. A method for assessing cardiac risks in a specific patient based on heart rate variability, comprising:
  providing heart activity data of a specific patient including a windowed time series related to heart rate variability during a heart rate test;
  determining a frequency domain value based on energy values of frequency bands of the heart rate variability in the windowed time series;

determining an aggregate power for a frequency band of the windowed time series; and assessing the risk of a cardiac event based on the frequency value and the aggregate power;

wherein providing heart activity data comprises determining an instantaneous heart rate sequence from an ECG waveform obtained during an exercise period of increasing heart rate and a recovery period of decreasing heart rate, providing a uniform sample series of the instantaneous heart rate sequence, and reducing the uniform sample series to obtain a heart rate variability waveform associated with variances in the heart rate between beats in a desired frequency band.

24. The method of claim 23 wherein: determining an instantaneous heart rate sequence comprises ascertaining R-R intervals of the ECG waveform and expressing the instantaneous heart rate sequence in beats/minute; reducing the uniform sample series comprises processing the uniform sample series through a selected band filter that provides the heart rate variability waveform for selected frequencies; performing a Fourier transform of the windowed time series into a spectrum for frequency domain analysis; and computing an aggregate power of the windowed time series using a root-means-square computation.

25. The method of claim 23 wherein: determining an instantaneous heart rate sequence comprises ascertaining R-R intervals of the ECG waveform; providing a uniform sample series of the instantaneous heart rate sequence comprises interpolating between adjacent beats at a uniform sample rate; and reducing the uniform sample series comprises processing the uniform sample series through a selected band filter that provides the heart rate variability waveform for selected frequencies.

26. The method of claim 23 wherein reducing the uniform sample series comprise forward filtering through at least a portion of the exercise period of the heart rate test to approximately an end of a peak exercise phase and reverse filtering through at least a portion of the recovery period of the heart rate test to approximately the end of the peak exercise phase.

27. A method for assessing cardiac risks in a specific patient based on heart rate variability, comprising:
providing heart activity data of a specific patient including a windowed time series related to heart rate variability during a heart rate test;
determining a frequency domain value based on energy values of frequency bands of the heart rate variability in the windowed time series;
determining an aggregate power for a frequency band of the windowed time series; and
assessing the risk of a cardiac event based on the frequency value and the aggregate power;
wherein the energy values comprise a low frequency average power, a middle frequency average power, and a high frequency average power of the windowed time series, and wherein determining the frequency domain value comprises (a) fitting a line to the low frequency average power, the middle frequency average power, and the high frequency average power, and (b) determining a slope of the line to obtain a spectral slope, wherein the frequency domain value comprises the spectral slope.

28. The method of claim 27 wherein assessing the risk of a cardiac event comprises comparing the determined frequency domain value with a reference frequency domain value range associated with a population that has experienced the cardiac event.

29. A method for assessing cardiac risks in a specific patient based on heart rate variability, comprising:
providing heart activity data of a specific patient including a windowed time series related to heart rate variability during a heart rate test;
determining a frequency domain value based on energy values of frequency bands of the heart rate variability in the windowed time series;
determining an aggregate power for a frequency band of the windowed time series; and
assessing the risk of a cardiac event based on the frequency value and the aggregate power;
wherein providing the heart activity data comprises: identifying a peak exercise phase and a mid-recovery phase of the heart rate test; determining instantaneous heart rate sequences for the peak exercise phase and the mid-recovery phase by ascertaining R-R intervals of an ECG waveform of the peak exercise phase and the mid-recovery phase; providing uniform sample series of the instantaneous heart rate sequences by interpolating between adjacent beats at a uniform sample rate; and reducing the uniform sample series by filtering the uniform sample series through a selected band filter in a forward direction through at least the exercise period and in a reverse direction through at least a portion of the recovery period to provide the heart rate variability waveform for selected frequencies during the peak exercise phase and the mid-recovery phase.

30. The method of claim 29 wherein the aggregate power comprises a sum of the power of the spectral components within the selected frequency band.

31. The method of claim 30 wherein assessing the risk of a cardiac event comprises comparing (a) a difference between the determined peak exercise frequency domain value and the determined mid-recovery exercise frequency value with (b) a difference between a reference peak exercise frequency domain value range associated with a population that has experienced the cardiac event and a reference mid-recovery frequency domain value range associated with the population that has experienced the cardiac event.

32. A method for assessing cardiac risks in a specific patient based on heart rate variability, comprising:
providing heart activity data of a specific patient including a windowed time series related to heart rate variability during a heart rate test;
determining a frequency domain value based on energy values of frequency bands of the heart rate variability in the windowed time series;
determining an aggregate power for a frequency band of the windowed time series; and
assessing the risk of a cardiac event based on the frequency value and the aggregate power;
wherein determining an aggregate power comprises performing a root-means-squared calculation of a corresponding windowed time series.

33. The method of claim 32 wherein assessing the risk of a cardiac event comprises comparing the determined aggregate power with a reference aggregate power range associated with a population that has experienced the cardiac event.

34. The method of claim 32 wherein assessing the risk of a cardiac event comprises (a) comparing the determined frequency domain value with a reference frequency domain value range associated with a population that has experienced the cardiac event and (b) comparing the determined aggregate power with a reference aggregate power range associated with the population that has experienced the cardiac event.

35. An apparatus for assessing cardiac risks in a specific patient based on heart rate variability, comprising:

at least one sensor configured to obtain cardiac signals from a specific patient; and a computer configured to receive the cardiac signals from the sensor, and the computer including a computer operable medium having instructions that cause the computer to (a) provide heart activity data of the specific patient including a windowed time series related to heart rate variability during a heart rate test, (b) determine a frequency domain value based on at least one of energy values of frequency bands and spectral slope(s) across selected frequency ranges of the heart activity data in the windowed time series, and (c) assess the risk of a cardiac event based on the frequency domain value; wherein the heart activity data comprises an instantaneous heart rate sequence from an ECG waveform obtained during an exercise period of increasing heart rate and a recovery period of decreasing heart rate, and the instructions cause the computer to provide a uniform sample series of the instantaneous heart rate sequence, and reduce the uniform sample series by filtering and/or detrending via fitting a polynomial function to the heart activity data across a selected time window to obtain a heart rate variability waveform associated with variances in the heart rate between beats in a desired frequency band.

* * * * *